(12) United States Patent
Hebler et al.

(10) Patent No.: US 10,095,838 B2
(45) Date of Patent: Oct. 9, 2018

(54) GRAPHICAL PRESENTATION OF EWS/PATIENT STATE

(75) Inventors: Sebastian Hebler, Herrenberg (DE); Guenter Gegner, Tuebingen (DE); Wilhelm Meier, Herrenberg (DE); Gerhard Tivig, Nufringen (DE); Bernd Steffen Heiner Gaertner, Holtzgerlingen (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 657 days.

(21) Appl. No.: 13/550,667

(22) Filed: Jul. 17, 2012

(65) Prior Publication Data

US 2013/0027411 A1 Jan. 31, 2013

Related U.S. Application Data

(60) Provisional application No. 61/512,934, filed on Jul. 29, 2011.

(51) Int. Cl.
*G16H 50/30* (2018.01)
*G16H 15/00* (2018.01)
*G06F 19/00* (2018.01)

(52) U.S. Cl.
CPC .......... *G06F 19/3418* (2013.01); *G06F 19/00* (2013.01); *G16H 50/30* (2018.01); *G16H 15/00* (2018.01)

(58) Field of Classification Search
CPC .......... G06F 19/3406; G06F 19/3431
USPC ....................................................... 345/440
See application file for complete search history.

(56) References Cited

U.S. PATENT DOCUMENTS

| 8,092,380 | B2 * | 1/2012 | Rothman et al. ............. 600/300 |
| 8,403,847 | B2 | 3/2013 | Rothman et al. |
| 8,412,655 | B2 * | 4/2013 | Colman et al. ................. 706/16 |
| 8,510,126 | B2 * | 8/2013 | Martin et al. ..................... 705/2 |
| 2002/0178032 | A1 * | 11/2002 | Benn ...................... A61C 19/00 705/2 |
| 2003/0093125 | A1 * | 5/2003 | Zhu ...................... A61N 1/3627 607/25 |

(Continued)

FOREIGN PATENT DOCUMENTS

| EP | 2093683 A2 | 8/2009 |
| WO | 2008045577 A2 | 4/2008 |
| WO | 2009015466 A1 | 2/2009 |

OTHER PUBLICATIONS

Smith, G. B., et al.; Hosptial-wide physiological surveillance—A new approach to the early identification and management of the sick patient; 2006; Resuscitation; 71:19-28. Oct. 2006.

(Continued)

*Primary Examiner* — Joni Richer (57) ABSTRACT

A patient monitoring system includes a display that displays a plurality of sectors including one or more icons. A controller is configured to display patient data received from a patient monitoring system in a corresponding sector of the display. The controller programmed to determine patient status from the patient data and display the patient status as an icon on the display. The icon is color-coded with the severity or deviation from normal of the patient status. The icon can also include an arrow that indicates if the patient status is improving or deteriorating.

15 Claims, 5 Drawing Sheets

(56) References Cited

U.S. PATENT DOCUMENTS

| | | | |
|---|---|---|---|
| 2003/0149450 A1* | 8/2003 | Mayberg | A61N 1/08 607/3 |
| 2006/0206013 A1 | 9/2006 | Rothman et al. | |
| 2007/0219823 A1* | 9/2007 | Warner | G06F 19/3418 705/2 |
| 2008/0214904 A1 | 9/2008 | Saeed et al. | |
| 2009/0037220 A1* | 2/2009 | Chambers | G06F 19/3418 705/3 |
| 2009/0093686 A1 | 4/2009 | Hu et al. | |
| 2009/0216556 A1 | 8/2009 | Martin et al. | |
| 2010/0083164 A1 | 4/2010 | Martin et al. | |

OTHER PUBLICATIONS de Jager, D., et al.; A Low-Power Simplified-MEWS Scoring device for Patient Monitoring; 2010; Pervasive Computing Technologies for Healthcare (Pervasive Health) 4th International Conference; 4 pages,Mar. 2010.

* cited by examiner

GRAPHICAL PRESENTATION OF EWS/PATIENT STATE

CROSS REFERENCE TO RELATED APPLICATIONS

This application claims the benefit of U.S. provisional application Ser. No. 61/512,934 filed Jul. 29, 2011, which is incorporated herein by reference.

DESCRIPTION

The present application relates generally to patient monitoring. It finds particular application in conjunction with the graphical presentation of Early Warning Scoring (EWS) information and will be described with particular reference thereto. However, it is to be understood that it also finds application in other applications, and is not necessarily limited to the aforementioned application.

Patient deterioration is often preceded by a period of abnormal vital signs. Therefore, clinicians often manually assess the risk of patient deterioration using an abnormality scoring system, such as Early Warning Score (EWS) scoring or Modified EWS (MEWS) scoring systems. Abnormality scoring systems unify assessments of a plurality of vital signs into a unified unit system and combine the individual assessments so as to determine a score of the risk of a patient, which may lead to preventable adverse events like cardiac arrest or death. Patient deterioration is also assessed by Single Parameters Score (SPS) schemes that identify patients with physiological abnormalities and trigger subsequent calls to Rapid Response Teams (RRTs) for rapid and appropriate patient management.

Presently, central station or other multi-patient monitoring devices have a fixed area of a display assigned to each patient. The monitoring sectors include a plurality of sectors and icons which display various types of patient information. Each sector typically is populated by several icons that display the patient's identification, EWS score, SPS status, alarms, physiological parameters, such as an ECG signal, a respiration signal, pulse rate, blood pressure, SpO2, other indicators of patient health or well being, and the like. As more physiological parameters are monitored, the EWS score is often "lost" amongst the other patient information being displayed. As a result, it is often difficult for clinicians to identify patient deterioration and recognize the manner of change in the patient EWS score.

The present application provides a new and improved patient monitoring device which overcomes the above-referenced problems and others.

In accordance with one aspect, a patient monitoring system is provided. A display displays a plurality of sectors including one or more icons. A controller displays patient data received from a patient monitoring system in a corresponding sector of the display. The controller programmed to determine patient status with the patient data and display the patient status as an icon on the display.

In accordance with another aspect, a method of displaying medical parameters is provided. The method includes receiving patient data from a patient monitoring system, comparing the received patient data with preselected thresholds indicative of levels of deviation from normal, determining a patient status from comparing the received patient data with the preselected thresholds, controlling a display to display patient data received from a patient monitoring system in a corresponding sector of a display, and controlling the display to display a patient status icon.

One advantage resides in the fast and easy identification of patient deterioration.

Another advantage resides in the clear and easy recognition of change in patient status.

Another advantage resides in having the EWS score automatically calculated which avoids calculation errors, leads to more complete patient records, and reduces the time to compute MEWS manually.

Another advantage resides in having all data stored safely for later consultation.

Another advantage resides in the easy and fast identification of parameters outside a normal range and the amount of deviation from the normal range.

Still further advantages of the present invention will be appreciated to those of ordinary skill in the art upon reading and understand the following detailed description.

The invention may take form in various components and arrangements of components, and in various steps and arrangements of steps. The drawings are only for purposes of illustrating the preferred embodiments and are not to be construed as limiting the invention.

Figure 1:
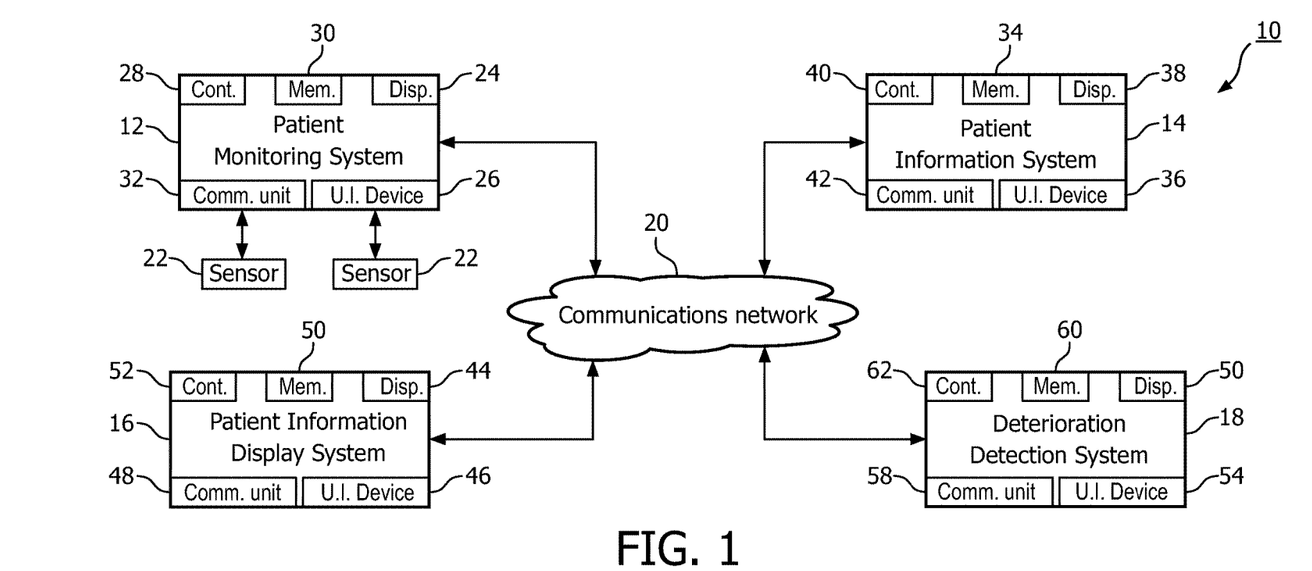
FIG. 1 is a block diagram of an IT infrastructure in accordance with the present application.

With reference to FIG. 1, a block diagram illustrates one embodiment of an information technology (IT) infrastructure 10 of a medical institution, such as a hospital. The IT infrastructure 10 suitably includes one or more patient monitoring systems 12, a patient information system 14, one or more patient information display systems 16, a deterioration detection system 18, and the like, interconnected via a communications network 20. It is contemplated that the communications network 20 includes one or more of the Intranet, a local area network, a wide area network, a wireless network, a wired network, a cellular network, a data bus, and the like.

The patient monitoring systems 12 obtain physiological data for patients (not shown) cared for by the medical institution. The physiological data is obtained automatically indicative of measurements of physiological parameters (or vital signs) of the patients, such as heart rate, temperature, blood oxygen saturation, and the like. Typically, each of the patient monitoring systems 12 is associated with, and obtains physiological data for, a single patient, but patient monitoring systems associated with multiple patients are contemplated. In some embodiments, it is contemplated that the patient monitoring systems 12 include patient worn monitors and/or beside monitors. The physiological data is typically obtained continuously or intermittently. When the physiological data is obtained continuously or frequently, a trending algorithm (e.g., average, median, peak-finding, etc.) is applied, in one embodiment, to break the stream of physiological data into discrete blocks of physiological data. For example, a continuous stream of physiological data can be separated into blocks of a predetermined duration and a trending algorithm can be applied to each block.

One or more sensors 22 suitably obtain the physiological data. However, it is also contemplated that the physiological data is obtained from other components of the IT infrastructure 10, such as lab equipment, components with user input devices, and so on. The sensors 22 measure physiological parameters of the patients and generate physiological data indicative thereof. In some embodiments, the sensors 22 include one or more electrocardiographic (ECG) electrodes, blood pressure sensors, SpO2 sensors, pulse sensors, thermometers, respiratory sensors, exhaled gas sensors, noninvasive blood pressure (NBP) sensors, and the like. Typically, the sensors 22 are disposed on the person of a patient and external to the patient monitoring systems 12. However, sensors local to the patient monitoring systems are contemplated. Where the sensors 22 are external, the physiological data can be obtained via a databus, such as a serial bus, a universal serial bus (USB), or the like; a body coupled network; a Bluetooth, a ZigBee, a wired or a wireless network; a medical body area network (MBAN); or the like.

In some embodiments, the patient monitoring systems 12 further obtain patient data for patients cared for by the medical institution. Patient data includes the physiological data and patient scores, such as an early warning score (EWS) or a modified early warning score (MEWS). The physiological data can further include manual assessments of physiological parameters of the patient, such as level of consciousness, concern, pain, urine output, and other data pertaining to physiological parameters that cannot be measured by one of the sensors, and/or manual measurements of physiological parameters, such as temperature, respiration rate, and so on input by clinicians. For example, the patient monitoring system 12 can indicate to a clinician whether manual entry of physiological data is needed to be entered. Once all of the mandatory physiological data is entered, a MEWS scores is calculated by the patient monitoring system 12 and EWS recommendations are displayed.

A patient score assesses the current status of the patient (or, in extreme conditions, the risk of death of a patient) and is obtained through calculation using the physiological data and a scoring table of physiological parameters. Suitably, the physiological data includes measurements for each physiological parameter of the scoring table. However, physiological data including fewer than all of the physiological parameters of the scoring table are contemplated. Scoring tables are completely user configurable, and no assumption regarding the used parameters and scoring thresholds are made. In some embodiments, the patient monitoring systems 12 facilitate the generation of a patient score. For example, it is contemplated that a process in a processor-based controller 28 of the patient monitoring systems 12 automatically calculates a patient score based on obtained physiological data and patient data and a scoring table. As another example, it is contemplated that the patient monitoring systems 12 merely provide a clinician with the scoring table and/or the physiological data, thereby leaving it to the clinician to calculate the patient score and input it into the relevant patient monitoring system via the user input devices 26.

The scoring table is suitably obtained from a remote component of the IT infrastructure 10, such as the patient information system 14, the patient information display systems 16, or the deterioration detection system 18, via the communications network 20. In such embodiments, a graphical user interface displayed on the remote component can be employed to facilitate selection and/or definition of the scoring table. However, it also is contemplated the scoring table is obtained from one or more memories 30 of the patient monitoring systems 12 and/or selected and/or defined by a clinician via the user input devices 26. As to selection and/or definition, a graphical user interface on the displays 24 of the patient monitoring systems 12 can be employed to facilitate selection and/or definition of the scoring table. Regardless of where the scoring table is obtained from, the scoring table is suitably selected and/or defined individually for each patient based on attributes of the patient, such as illness and/or history.

Figure 2:
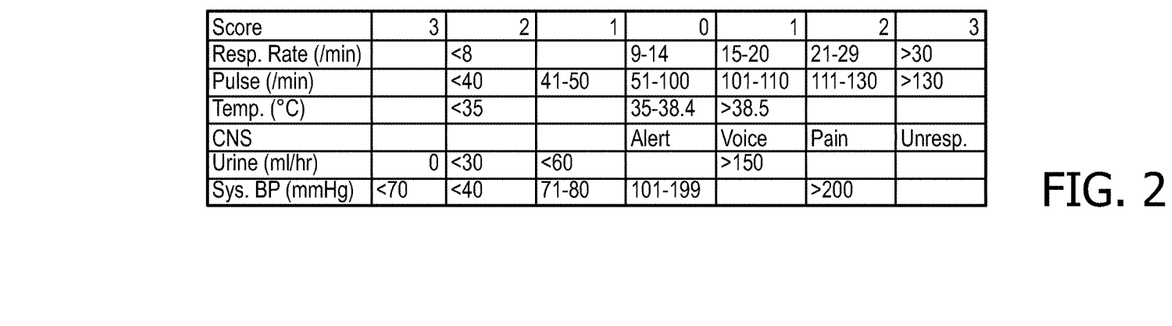
FIG. 2 is a table illustrative of a EWS scoring system.

With reference to FIG. 2, an example of a scoring table for determining a patient EWS score is provided. The first column identifies physiological parameters employed to calculate a patient score, and the first row identifies a sub-score to attribute to measured values of physiological parameters. Each of the cells, other than the cells of the first row and the first column, is associated with the physiological parameter of its row of the cell and the sub-score of the column of the cell. Even more, each of the cells, other than the cells of the first row and the first column, includes a range of measured values for the physiological parameter and sub-score associated with the cell. A sub-score for a measured value of a physiological parameter is determined by matching the value to a cell in the row associated with the physiological parameter and having a range matching the value. The patient EWS score is thus determined by summing the sub-scores of each of the measured values in the physiological data, or using the worst case of the individual sub-scores or other rule definitions defined by the scoring schema (e.g., aggregated MEWS and single parameter score).

Referring back to FIG. 1, in addition to relaying patient data and/or physiological data, the patient monitoring systems 12 monitor the patients based on the received patient data and/or physiological data and/or update associated displays to graphically present the patient data and/or physiological data to clinicians. As to the former, when patient data and/or physiological data indicates a patient needs medical attention due to, for example, increasing and/or decreasing respiration rate or blood pressure, the patient monitoring systems 12 that received the patient data and/or physiological data typically generates audio and/or visuals alerts and/or messages notifying clinicians thereof. It is contemplated that message can be provided to the clinicians via the communications network 20.

To carry out the above noted functionality, the sensors 22 transmit the measured physiological data via a body coupled network, Bluetooth, wired or wireless network, or the like to a controller 28 of the patient monitoring systems 12. The patient monitoring systems 12 serves as a gathering point for the patient data and/or physiological data measured by sensors 22 and provides temporary storage for the data in a memory 30. The collected physiological data is concurrently transmitted to a controller 28 in the patient monitoring systems 12 which then transmit the physiological data through the communication network 20 to the patient information system 14 where the physiological data is displayed and stored. The controller 28 of the patient monitoring systems 12 also controls a display 24 to display the measured physiological data received from each of the sensors 22 in the corresponding patient monitoring system display 24. Along with displaying the physiological data, the controller 28 also displays the patient data such as the EWS or MEWS scores. The controller 28 displays the patient data such that the patient data is presented to indicate the patient state and deterioration to the clinician. For example, the controller 28 displays an EWS score icon indicating the EWS or MEWS score as a numerical value (e.g. "7") with a color coded severity of the associated risk (e.g. "Urgent" risk band is red colored) allowing for fast and easy identification of patient state and deterioration. The EWS score icon utilizes a symbol including the MEWS score and is colored based upon the risk band severity. It is also contemplated that the controller 28 displays a EWS sub-score icon indicating the contribution of the culprit physiological parameters making up the EWS score to the total MEWS score. For example, the EWS sub-score icons also include the value with the number of points associated with the physiological parameter and is colored based upon the MEWS threshold range the value falls within. In the case of a MEWS scoring scheme, the underlying EWS scoring table dictates the sub-score associated with each measured or manually entered value (e.g. a sub-score of "1" is assigned if the Pulse Values are in the range of 101 to 110 bpm). The EWS sub-score icon also follows the color coding severity (e.g. a "1" indicates the "Observe-At risk" value range and has a yellow severity). This allows for easy identification of parameters that are outside the "normal" range and how these physiological parameters contributed to the overall MEWS score. This also allows for mixed MEWS scoring scheme and one or more SPS parameters to replicate hospital specific RRT workflow. This also It also contemplated that the controller 28 displays a EWS deterioration arrow indicating when an individual parameter (part of the MEWS scoring scheme) sub-score is worsening. Some physiological parameters increasing in value show improvements, such as abnormally low blood pressures going up. Other parameters decreasing in value show improvements, such as high blood pressure dropping. For ease of quick comprehension, up arrows indicate improvement and down arrows represent deteriorations regardless whether the absolute parameter values are getting bigger or smaller.

The color of the EWS deterioration arrow is based upon the sub-score severity of the afferent parameter. The colored arrow shows not only the direction of change but also indicates the sub-score severity reached with the measurement deviation from the agreed "normal" range. The patient information system 12 also includes an input device 22 that allows the user, such as a system administrator or clinician, to view, manipulate, and input patient data and physiological data displayed on the display 14. The input device 16 can be a separate component or integrated into the display 14 such as with a touch screen monitor. Where the patient monitoring systems 12 are operative to relay physiological data and patient data over the communications network 20, the patient monitoring systems 12 further include one or more communications units 32 facilitating communication between the controllers 28 and the communications network 20.

The patient information system 14, such as a central record medical database, receives patient data and/or physiological data for the patients and stores the data in one of one or more memories 34 thereof. Typically, the data is received from components of the IT infrastructure 10, such as the patient monitoring systems 12 and/or the patient information display systems 16, via the communications network 20. However, it is also contemplated that the data is received via one or more user input devices 36 of the patient information system 14. The patient information system 14 also includes a display 38 to display the patient data and physiological data as described above. In some embodiments, the patient information system 14 further displays and/or allows manipulation of the patient data and/or physiological data in the memories 34 using the user input devices 36 and/or the display 38. Additionally or alternatively, in some embodiments, the patient information system 14 further allows components of the IT infrastructure 10 to access the data in the memories 34 via the communications network 20. Where the patient information system 14 is operative to receive physiological data from the communications network 20, the patient information system 14 further includes one or more communications units 42 facilitating communication between the controllers 40 and the communications network 20.

The patient information display systems 16 receive patient data and/or physiological data for the patients cared for by the medical institution over the communications network 20 from a component of the IT infrastructure 10, such as the patient monitoring systems 12 and/or the patient information system 14. Typically, each of the patient information display systems 16 receives patient data and/or physiological data for a plurality of patients, but a patient information display system that receives patient and/or physiological data for a single patient is contemplated. Using the received data, the patient information display systems 16 monitor the patients and/or update associated displays 44 to display the physiological data and patient data to clinicians. As to the former, the patient data is displayed to indicate the patient state and deterioration to the clinician as described above.

In some embodiments, the patient information display systems 16 further allows clinicians to input patient data via one or more user input devices 46. It is contemplated that graphical user interfaces presented on the displays 44 can be employed to make it easier for the clinicians to enter the data. Upon inputting patient data, the patient data is suitably relayed to the patient information system 14 and/or other components of the IT infrastructure 10, such as the deterioration detection system 18, via the communications network 20. Additionally or alternatively, in some embodiments, the patient information display systems 16 include one or more of nursing stations, bedside monitors, mobile patient information displays, a deterioration detection station, a PDA, a tablet computer, a pager, and the like.

The deterioration detection system 18 obtains patient data and physiological data for the patients from components of the IT infrastructure 10, such as the patient information system 14 and/or the patient monitoring systems 12, and/or one or more user input devices 54 of the deterioration detection system 18, and tracks the most recent patient physiological data for each of the patients. The patient data is typically obtained when clinicians make ward rounds and need not be received at predefined intervals. It is also contemplated that patient data is obtained from patients being continuously monitored or from spot-check measurements done periodically during a non-attended mode. In that regard, the patient data can be obtained asynchronously. Further, the patient data suitably represents a complete assessment of the patient for which it relates. In other words, physiological data of patient data suitably includes measurements for each of the physiological parameters employed by the scoring table used to generate the patient score of the patient data.

In some embodiments, upon obtaining patient data, it is compared against previously obtained patient data to detect deterioration. It is contemplated that this can be performed through comparison of the patient scores or through comparison of individual physiological parameters, as described below. It is also contemplated that the deviation of the deterioration is also measured from the comparison. Additionally or alternatively, in some embodiments, a plurality of retrospective patient data is obtained at the same time. For example, the patient monitoring systems 12 buffered the retrospective patient data until a connection to the communications network 20 was available such that the buffered data can be viewed at a retrospective consultation. In such embodiments, the patient data can be compared to detect deterioration. Insofar as deterioration is detected, varying actions can be taken based upon the degree of difference between the scores. Actions include one or more of generating an audio and/or visual alert of patient deterioration, logging the deterioration in a database, sending a message and/or page to a clinician via, for example, the communications network 20, and so on. In some embodiments, the patient deterioration system 108 further includes the user input devices 144 and/or the display 146 allowing a clinician to manually enter patient data and/or other parameters employed by the deterioration detection system 108. Optionally, the patient monitoring systems 12, the patient information system 14, and the patient information display system 16 include a deterioration detection unit which obtain the patient data and physiological data from the IT infrastructure 10 and detects patient deterioration.

The patient monitoring system 12, patient information system 14, and patient information display system 16, and deterioration detection system 18 include at least one processor, for example a microprocessor or other software controlled device configured to execute patient monitoring software for performing the operations described in further detail below. Typically, the patient monitoring software is carried on tangible memory or a computer readable medium for execution by the processor. Types of non-transitory computer readable media include memory such as a hard disk drive, CD-ROM, DVD-ROM, internet servers, and the like. Other implementations of the processor are also contemplated. Display controllers, Application Specific Integrated Circuits (ASICs), FPGAs, and microcontrollers are illustrative examples of other types of component which may be implemented to provide functions of the processor. Embodiments may be implemented using software for execution by a processor, hardware, or some combination thereof.

Figure 3:
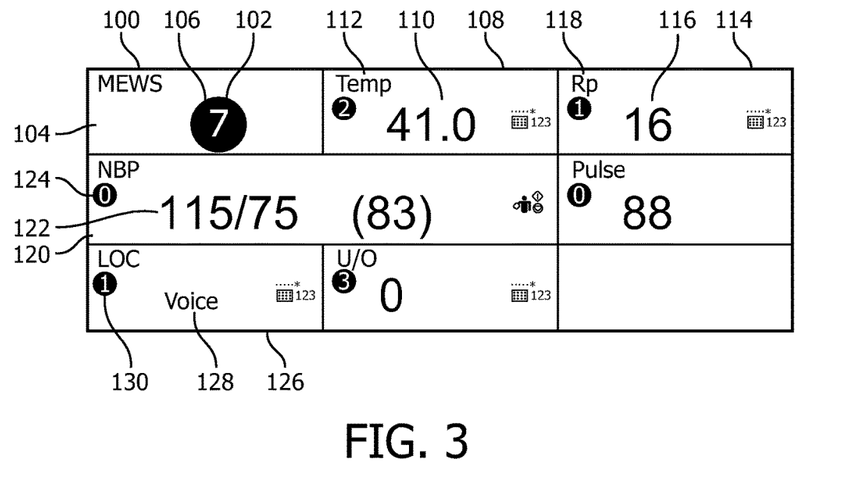
FIG. 3 is an exemplary illustration of a display including a EWS protocol with a EWS scoring icon and EWS sub-score icons.

As mentioned previously, controllers 28, 40, 52 direct the displays 24, 38, 44 of the patient monitoring system 12, patient information system 14, and patient information display system 16 to display the physiological data and patient data received from the IT infrastructure 10. With reference now to FIG. 3, a display including a EWS protocol with a EWS scoring icon and EWS sub-score icons is illustrated. The display 24, 38, 44 of the patient monitoring system 12, patient information system 14, and patient information display system 16 is divided into sectors 100, each sector 100 representing physiological and patient data received from or corresponding to one patient. Nine sectors 100 (only eight displaying information) are illustrated in FIG. 2, but more or fewer sectors are also contemplated. The number and size of sectors 100 could be dictated by the size of the display 24, 38, 44, the patient to patient information display system 10 ratio, the number of patients, the significance of the information, and other factors. As illustrated, each of the sectors 100 of the display 24, 38, 44 corresponds to physiological and patient data associated to a patient.

The sectors 100 of the display 24, 38, 44 include a plurality of icons 102 corresponding to the physiological and patient data received from the patient information system 14 or the patient monitoring system 12. A MEWS sector 104 includes a MEWS score icon 106 which indicates the patient's EWS or MEWS score as a numerical value (e.g. "7"). The MEWS score icon 106 is also color coded based on the severity of the EWS score. For example, an urgent EWS score would be identified by a red color code, an at risk EWS score would be identified by a yellow color code, a warning risk ban severity would be identified by a orange color code, a normal EWS score would be identified by a green or white color code, and the like. Other color codes can be associated with particular EWS scores, and not all of the above-mentioned color codes have to be associated with a EWS score at any given time. The EWS score icon 106 drives user attention to the calculated EWS or MEWS score and provides a clear and easy manner to recognize changes in the patient status. As changes are made to the EWS or MEWS score, the score is dynamically updated to reflect the change in the patient status. Optionally, an improvement/deterioration indicator can also be displayed. For example, an up arrow can show that the MEWS value is improving over time and a down arrow can show deterioration.

A temperature sector 108 includes a temp icon 110 that displays the latest temperature readings received from the patient information server 14 or patient monitoring system 12 about the patient. The temperature sector 108 also includes a EWS sub-score icon 112 which indicates the sub-score associated with the measured or manually entered temperature value (e.g. a sub-score of "2" is assigned if the temperature values are greater than 38.6). The sub-score icon 112 also includes the severity color code (e.g. a "2" indicates the "At risk" value range and has a yellow severity). This allows for easy identification of which parameters are outside the "normal" range and how the parameter contributes to the overall EWS or MEWS score. The "EWS sub-score" icon 112 also indicates the amount the measure value deviates from the "normal" range. It also allows the nurse or nurse assistant from the general floor to trace back the MEWS calculation. Optionally, an improvement/deterioration indicator can also be included.

A respiratory sector 114 include a respiratory rate icon 116 that displays the latest respiratory rate received from the patient information server 14 or patient monitoring system 12 about the patient and an EWS sub-score icon 118 which indicates the sub-score associated with the respiratory rate. A blood pressure sector 120 include s a blood pressure icon 122 that displays the latest blood pressure reading from the patient and an EWS sub-score icon 124 which indicates the sub-score associated with the blood pressure. There may also be a pulse sector, urine output sector, alarm sectors, waveform sectors, trend sectors, other physiological data sectors, historical data sectors, battery life sectors, and the like. Improvement/deterioration indicator can optionally be associated with some or all of the sectors. Other sectors 100 can be associated with the display, and not all of the above-mentioned sectors have to be associated with the display at any given time. Additionally, other icons 102 can be associated with a sector 100, and not all of the above-mentioned icons 102 have to be associated with a sector 100 at any given time. It should also be appreciated that not every sector includes a EWS sub-score icon. Some sectors do not display a component of the EWS or MEWS score. The sectors 100 can also display patient data that is entered by a clinician in a corresponding sector 100. A consciousness state sector 126 includes a consciousness icon 128 that displays the latest consciousness input by a clinician and a EWS sub-score icon 130 which indicates the sub-score associated with the consciousness of the patient.

Figure 4:
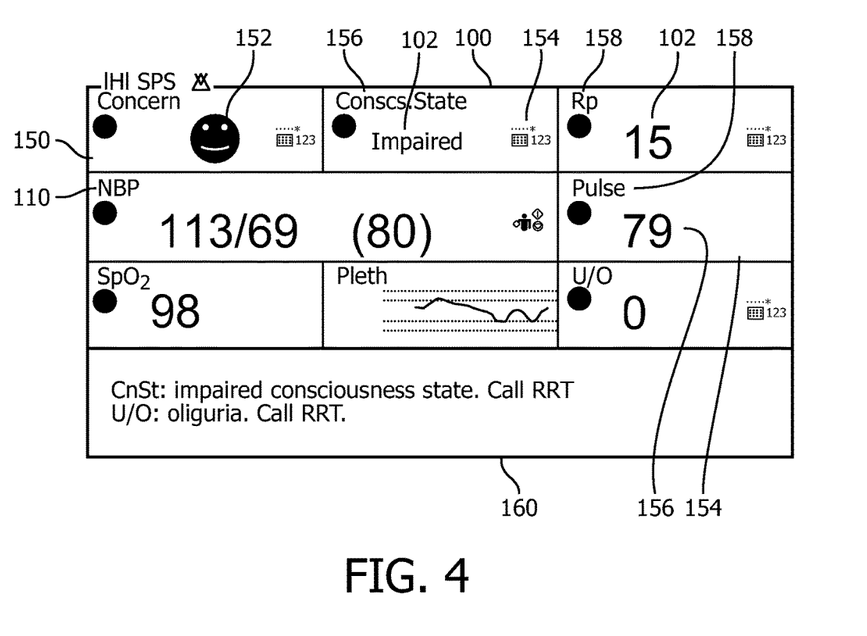
FIG. 4 is an exemplary illustration of a display including a EWS protocol with EWS sub-score icons for a SPS parameter scheme in accordance with the present application.

With reference to FIG. 4, a display including a EWS protocol with EWS sub-score icons for a single parameter score (SPS) is illustrated. The SPS scheme triggers a call to the RRT as soon as any of the measurements part of this SPS scheme gets out of the agreed "normal" range. The display allows for the easy and intuitive indication whether a measurement represents a SPS parameter. In this case, the EWS score and sub-score icons include a color code to indicate whether a deviation from "normal" range is present. For example, a measurement or score in the normal range could be identified by a white or other color code and a measurement or score outside the normal range could be identified by a red or other color code. The display 24, 38, 44 includes a plurality of sectors 100 and icons 102 as described above. A concern sector 150 includes a SPS icon 152 which indicates the patient's status based on the amount and degree of abnormality of SPS parameters. The SPS icon 152 is also color coded based on the status of the patient. For example, the patient status may be at risk when a predetermined amount of parameters are SPS parameters are outside a normal range. The icons can change other features to express concern such as the face with the illustrated smile for good, a straight mouth for mild concern, and a frown for a high level of concern.

Each of the sectors 154 include icons 156 which display the latest measurement corresponding to the sector received from the patient information server 14 or patient monitoring system 12 about the patient as described above. The sectors 154 also include a SPS icon 158 which indicate whether the measured parameter associated with the sector 152 is outside a normal range e.g. with color, faced features, or the like. The display also includes a SPS trigger sector 160 which disclose the SPS trigger events. In other words, the SPS trigger sector 160 indicates each of the measured parameters that are outside a normal range or which meet another pre-established criterion.

Figure 5:
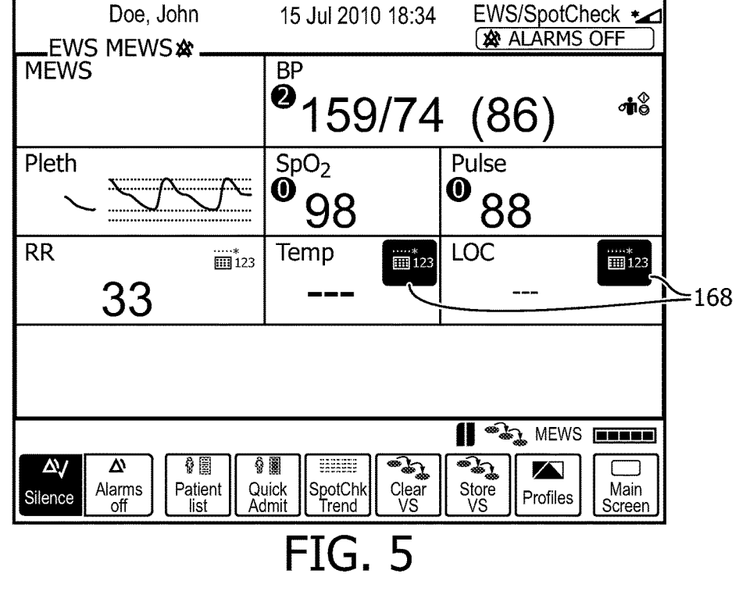
FIG. 5 is an exemplary illustration of a display including manual entry indicator.
Figure 6:
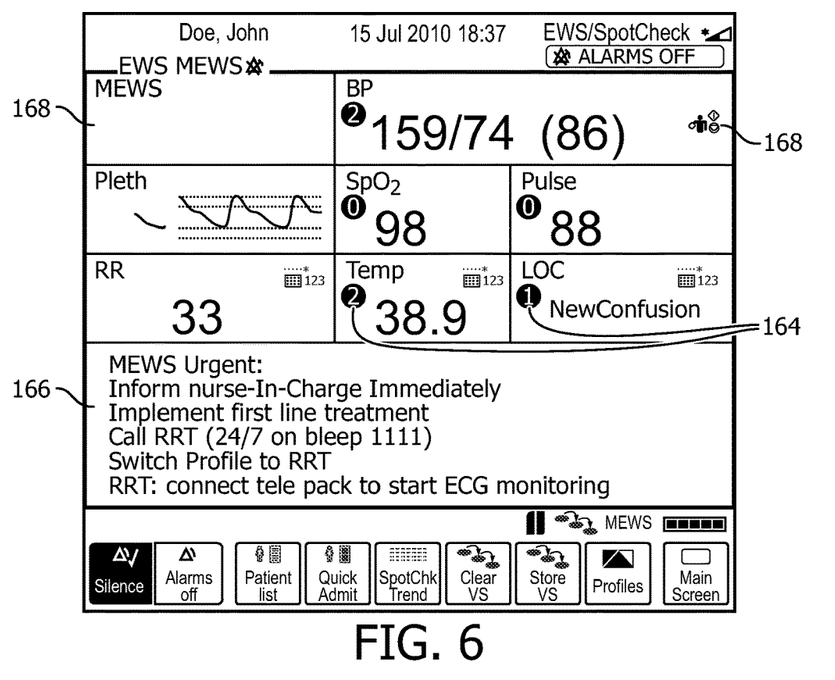
FIG. 6 is an exemplary illustration of a display including EWS recommendations in accordance with the present application.

With reference to FIG. 5, a display including a graphical indicator 162 to indicate to a clinician to manual enter physiological parameters is illustrated. The graphical indicator 162 indicates that physiological parameters are needed to be inputted in order for the EWS score to be calculated. For example, the temperature and LOC are mandatory parameters for the EWS Scoring and the graphical indicator 162 indicates to the clinician to enter these using the shown graphical symbol in the afferent sector as a rectangular full video numpad icon. As soon as the requested parameter is manually entered, this symbol reverts to a half intensity small numpad icon. FIG. 6 illustrates a display displaying the calculated EWS scores 164 and EWS recommendations 166 when all the mandatory physiological parameters are entered. The upper part of the EWS related sectors 168 gets a shaded gray color and the bottom part shows the actual recommendations 164 pertinent to the resulted MEWS risk band.

Figure 7:
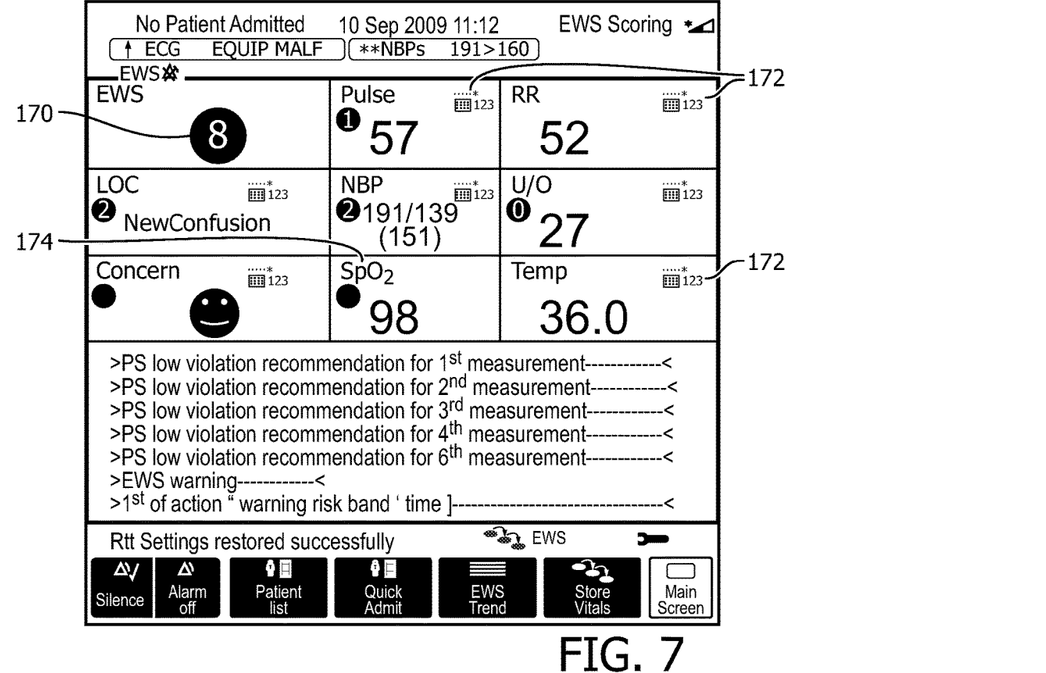
FIG. 7 is an exemplary illustration of a display including a combination MEWS scoring scheme and SPS parameter scheme in accordance with the present application.

With reference to FIG. 7, a display including a combination EWS scoring scheme 170, 172 and SPS parameter scheme 174 is displayed. For example, the EWS score 170 is shown with its input parameters Pulse, RR, LOC, NBP and U/O, and the like. Each of these parameters includes a sub-score icon 172 coding the number of points this parameter gets based upon the underlying MEWS scoring table. Additionally, the display displays a SpO2 parameter 174 is displayed as an SPS scoring parameter. The SPS scoring parameter 172 is either a white ("Normal") circle or an abnormal red ("Urgent") circle but does not includes a sub-score indication in it. It should also be appreciated that not every sector includes a EWS sub-score icon or a SPS scoring parameter.

Figure 8:
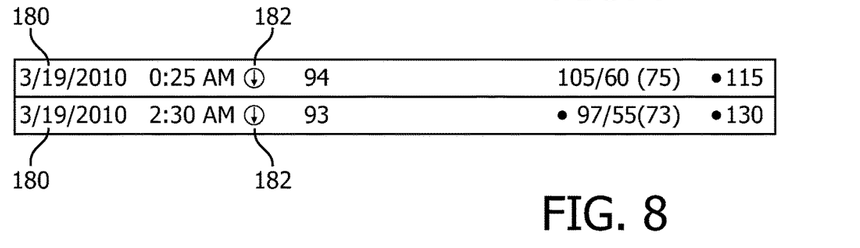
FIG. 8 is an exemplary illustration of a display including a EWS protocol with EWS Deterioration Arrows.

With reference to FIG. 8, a display including a EWS protocol with EWS deterioration arrows is illustrated. The display 24, 38, 44 includes sectors 180 that display a patient's physiological data and patient data for a particular time. The sectors 180 include a full or partial list of the physiological and patient data for the patient at the particular time, e.g. the data outside of the normal range. The sectors 180 also include a arrow 182 which indicates whether the patient's EWS or individual physiological data scores are improving (approaching normal) or deteriorating (diverting further from normal). The color of the arrow 182 is based upon the color coded severity of the EWS score as described above. It is also contemplated that the arrow 182 is used as an alert notification to indicate when an individual parameter (part of the MEWS Scoring scheme) sub-score is worsening. The color of the arrow 182 is based upon the sub-score severity of the afferent parameter. The colored arrow shows not whether the EWS or individual parameters is getting higher or lower, but whether the patient is improving (up) or deteriorating (down). The arrow 182 alert notification does not interfere with the basic alarming indications of a patient monitor. In the example of FIG. 8, the 0:25 measurements show a low SpO2 reading and a high pulse rate with a down arrow displayed in yellow. The 2:30 measurements show a lower SpO2 reading, an event more elevated pulse, plus blood pressure dropping below the normal range. Hence, the arrow is pointing down and displayed in red. The workflow in the general floor relies on the appropriate patient deterioration notifications derived from trended data as vital signs are collected on an intermittent base and basic alarming is not suitable.

Figure 9:
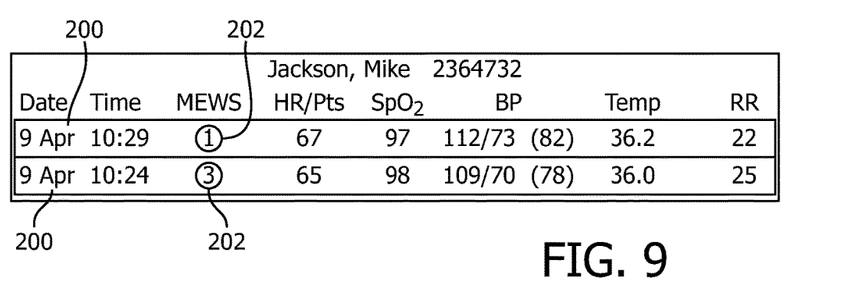
FIG. 9 is an exemplary illustration of a display including a EWS protocol with a EWS scoring icon in a single patient view in accordance with the present application.

With reference to FIG. 9, a display including a EWS protocol with a EWS scoring icon in a single patient view is illustrated. The display 24, 38, 44 includes sectors 200 that display a patient's physiological data and patient data for a particular time. The sectors 200 include a full or partial list of the physiological and patient data for the patient at the particular time. A MEWS icon 202 indicates the patient's EWS or MEWS score as a numerical value (e.g. "1" or "3"). The MEWS icon 202 is also color coded based on the severity of the EWS score as mentioned above. Note that between the 10:24 and the 10:29 measurements, the patient's heart rate, blood pressure, and respiratory rate improved leading to the MEWS icon changing from yellow to white and a lower MEWS score.

Figure 10:
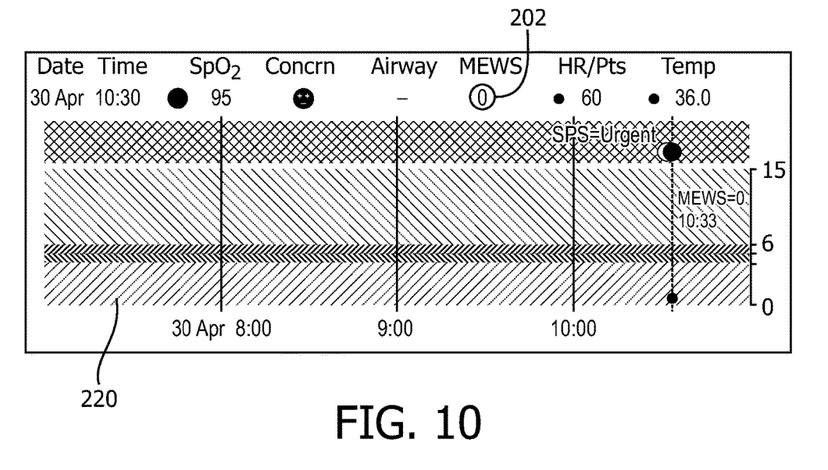
FIG. 10 is an exemplary illustration of a display including a MEWS graphical trend with a EWS scoring icon.

With reference to FIG. 10, a single set of a patient's data is shown. The display 24, 28, 44 illustrates a combination of physiological data with it sub-scores and their graphical trend presentation 220. The graphical trend is divided into two parts, a scale sub-risk band area showing the calculated MEWS score and further graphical information describing the patient's health status at a given time. Specifically, the display includes a MEWS graphical trend with a EWS scoring icon is illustrated. The display 24, 38, 44 include a graphical trend 220 of the MEWS score using the underlying risk band severities scale and indicating for each measurement the associated EWS sub-score icon 202. The graphical trend 220 tracks MEWS score over time and allows an easy and intuitive recognition of patient status deterioration.

Figure 11:
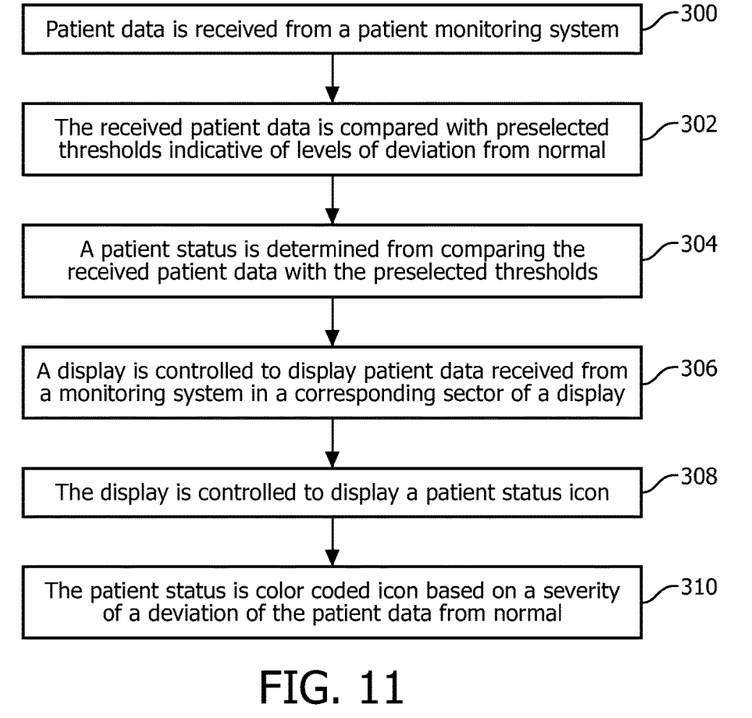
FIG. 11 is a flowchart diagram of the operation of a patient monitoring system in accordance with the present application.

FIG. 11 illustrates one example of steps performed by a processor in the controller 29 of the patient monitoring system 12. In a step 300, patient data is received from a patient monitoring system. In a step 302, the received patient data is compared with preselected thresholds indicative of levels of deviation from normal. In a step 304, a patient status is determined from comparing the received patient data with the preselected thresholds. In a step 306, a display is controlled to display patient data received from a patient monitoring system in a corresponding sector of a display. In a step 308, the display is controlled to display a patient status icon. In a step 310, the patient status is color coded icon based on a severity of a deviation of the patient data from normal.

In one embodiment for implementation of this application, the EWS protocol is implemented in a patient monitor. The graphical elements for EWS related information are elements of the EWS protocol and support the user in identifying changes in the patient state. Other embodiments implement the EWS protocol together with the graphical presentations of the EWS related information on a PC based Nurse Station or Central Station like system. The preferred embodiment can be used in various setups of a EWS protocol. MEWS scheme and SPS scoring scheme are also supported. The RRT calling workflow is supported by the possibility to combine the MEWS scheme with additional SPS parameters for initiating calls to the RRT. One of ordinary skill in the art will recognize that the EWS protocols are not only used in general and medical floors but also upon patient admission in Triage protocols or even in Intensive Care Units for critically ill patients monitored continuously.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

Having thus described the preferred embodiments, the invention is now claimed to be:

1. A patient monitoring device comprising:
   a display that displays a plurality of sectors including one or more icons;
   a controller configured to display patient data of a patient received from a patient monitoring device in a corresponding sector of the display, the controller programmed to:
   determine patient status with the patient data; and
   display the patient status as an icon on the display;
   color code the patient status icon based on a severity of the patient status;
   determine patient sub-scores from the patient data;
   display patient sub-scores icons in a corresponding sector; and
   color code the patient sub-scores icons based on the severity of the patient status; and
   wherein the severity is determined by comparing the received patient data against previously collected patient data of the patient, the previously collected patient data being buffered until a connection to a communication network becomes available.

2. The patient monitoring device according to claim 1, wherein the controller is further programmed to determine patient status indicative of at least one of an Early Warning Scoring (EWS) score and a Modified Early Warning Scoring (MEWS) score.

3. The patient monitoring device according to claim 1, wherein the patient data includes at least one of currently monitored physiological data and inputted clinical data.

4. The patient monitoring device according to claim 1, wherein the controller is further programmed to display a patient status deterioration arrow indicating deterioration or improvement in the patient status.

5. The patient monitoring device according to claim 4, wherein the controller is further programmed to color code the patient status deterioration arrow based on the severity of the patient status.

6. The patient monitoring device according to claim 1, wherein the controller is further programmed to:
   display a patient status trend trending the patient status against time.

7. A patient monitoring system, the system comprising:
   the patient information system which receives and displays patient data; and
   one or more of the patient monitoring devices according to claim 1.

8. A method of displaying medical parameters, the method comprising:
   receiving patient data of a patient from a patient monitoring system;
   comparing the received patient data with previously collected patient data of the patient;
   buffering the previously collected patient data until a connection to a communication network becomes available;
   determining a patient status from comparing the received patient data with the previously collected patient data;
   controlling a display to display patient data received from a patient monitoring system in a corresponding sector of the display;
   controlling the display to display a patient status icon;
   color coding the patient status icon based on a magnitude of change between the received patient data and the previously collected patient data;
   determining patient sub-scores from the patient data;
   displaying patient sub-scores icons in a corresponding sector; and
   color coding the patient sub-scores icons based on the severity of the patient status.

9. The method according to claim 8, wherein the patient status is indicative of at least one of an Early Warning Scoring (EWS) score and a Modified Early Warning Scoring (MEWS) score.

10. The method according to claim 8, further including:
    displaying a patient status deterioration arrow indicating whether the patient status is deteriorating or improving.

11. The method according to claim 8, further including:
    color coding the patient status deterioration arrow based on the severity of the patient status.

12. A non-transitory computer readable medium containing software which, when loaded into a processor, programs the processor to perform the method according to claim 8.

13. A patient monitoring station comprising:
    a display;
    an input via which physiological data is received; and
    one or more processors programmed to perform the method according to claim 8.

14. A display on a patient monitoring device comprising:
    a plurality of sectors;

one or more icons which display patient data of a patient received from a patient monitoring device in a corresponding one of the sectors and a patient status icon determined with the patient data;

wherein the patient status icon is color coded based on a severity of the patient status; and wherein the severity is determined by comparing the received patient data against previously collected patient data of the patient, the previously collected patient data being buffered until a connection to a communication network becomes available;

wherein patient sub-scores determined from the patient data are displayed in a corresponding sector on the display and color coded based on the severity of the patient status.

15. The display according to claim 14, wherein the patient status is indicative of at least one of an Early Warning Scoring (EWS) score and a Modified Early Warning Scoring (MEWS) score.

* * * * *